United States Patent [19]

Yoo

[11] 4,018,834

[45] Apr. 19, 1977

[54] HYDROCARBONYLATION OVER IRON ON SUPPORT HAVING SILICA ALUMINA DISPERSED IN A SEPARATE PHASE ALUMINA MATRIX

[75] Inventor: Jin Sun Yoo, South Holland, Ill.

[73] Assignee: Atlantic Richfield Company, Los Angeles, Calif.

[22] Filed: Feb. 13, 1976

[21] Appl. No.: 657,814

Related U.S. Application Data

[63] Continuation of Ser. No. 424,488, Dec. 13, 1973, abandoned, which is a continuation of Ser. No. 30,275, April 20, 1970, abandoned.

[52] U.S. Cl. .................. 260/632 HF; 260/604 HF; 252/459
[51] Int. Cl.² ........................................ C07C 45/04
[58] Field of Search ............ 424/488; 260/604 HF, 260/632 HF; 252/459

[56] References Cited

UNITED STATES PATENTS

| | | | |
|---|---|---|---|
| 2,497,303 | 2/1950 | Gresham | 260/604 HF |
| 3,352,924 | 11/1967 | Gladrow | 260/604 HF |

*Primary Examiner*—Bernard Helfin
*Assistant Examiner*—W. B. Lone
*Attorney, Agent, or Firm*—John R. Ewbank

[57] ABSTRACT

A separate phase of alumina is the matrix in which a separately prepared silica alumina is dispersed in the mixture of aqueous gels, which mixture is spray dried, and the solids calcined at about 1350° F for about 3 hours. From about 0.001% to about 0.1% iron is impregnated into the support. Hydrocarbonylation of pentene-1 over such iron-containing catalyst provides hexanol and hexanal with an attractive combination of activity, selectivity, and stability for the catalytic process, the iron remaining on the support after repeated leaching by liquid product.

3 Claims, No Drawings

HYDROCARBONYLATION OVER IRON ON SUPPORT HAVING SILICA ALUMINA DISPERSED IN A SEPARATE PHASE ALUMINA MATRIX

RELATED APPLICATIONS

This is a continuation of Ser. No. 424,488 filed Dec. 13, 1973 which was a continuation of Ser. No. 30,275, filed Apr. 20, 1970, both now abandoned.

This invention relates to a new solid catalyst composition suitable for the hydroformylation, including hydroxyhydroformylation, of low molecular weight olefins to form the corresponding aldehydes and alcohols.

Processes directed to the production of reaction mixtures comprising substantial amounts of aldehydes and at times lesser amounts of alcohols by the reaction of olefinic compounds with carbon monoxide and hydrogen at elevated temperatures and pressures in the presence of certain catalysts are well known in the art. The aldehydes and alcohols produced generally correspond to the compounds obtained by the addition of a carbonyl or carbinol group to an olefinically-unsaturated carbon atom in the starting material with simultaneous saturation of the olefin bond. Isomerization of the olefin bond may take place to varying degrees under certain conditions with the consequent variation in the products obtained. These processes known in the industry, and referred to herein as hydroformylation, involve reactions which may be shown in the general case by the following equation:

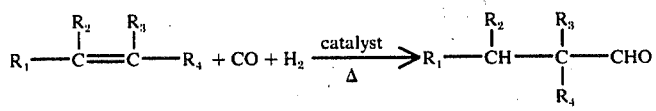

and/or

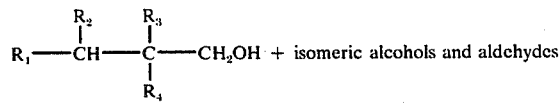

In the above equation, each R represents an organic radical, for example hydrocarbyl, or a suitable atom such as hydrogen or a halogen. The above reaction is similarly applied to an olefinic linkage in a cycloaliphatic ring.

In the past, iron pentacarbonyls as such or in several different forms generally have been used as the catalyst for the hydroformylation of olefins as is shown in U.S. Pat. Nos. 2,327,066 and 2,497,303. These catalysts which can be prepared from many forms of the metal, usually decomposes rapidly unless high pressures (1000–4500 p.s.i.g.) of carbon monoxide are maintained. Correspondingly high pressures of hydrogen are also necessary. The activities of these catalysts are poor. A most serious disadvantage of prior hydroformylation processes, however, has been the necessity of proceeding in two steps when alcohols are the desired product. Thus, in processes disclosed heretofore, it is generally necessary first to react the olefin to be hydroformylated with carbon monoxide and hydrogen to form the corresponding aldehyde. It is then necessary to carry out a second reaction with hydrogen to reduce the aldehyde to the alcohol in a separate operation. A different catalyst for the hydrogenation is usually needed for this second step since the hydroformylation catalysts heretofore employed are not sufficiently effective for this purpose. This results in the need for relatively expensive high-pressure equipment and for a large amount of such equipment to handle the two steps.

A further disadvantage inherent in processes directed to hydroformylation disclosed heretofore is a relative inability to direct the reactions involved the production theproduction of predominantly terminal alcohols when the olefin contains more than two carbon atoms, particularly when the charge to the process comprises primarily internal olefins.

It is an object of this invention, therefore, to provide a novel catalyst system for the hydroformylation, including hydroxyhydroformylation, of olefins. More specifically, it is an object of this invention to provide a novel, heterogeneous solid phase catalytic system for the hydroformylation of low molecular weight olefins to form the corresponding alcohols and aldehydes. A solid phase catalyst is highly desirable for a number of reasons, including the ease of handling of solids as contrasted with liquids. In addition, a solid catalyst could be more readily and completely separated from the low molecular weight alcohols and aldehydes commonly produced by such catalysts. When surface phenomena are considered, a solid phase catalyst might also be more active and more selective than the homogeneous solution type of the same general ingredients.

It has been found that iron, when hydrocarbonylated, on a solid, acidic, silica-based support, provides a solid phase composition having highly desirable physical and chemical characteristics and, particularly, excellent catalytic activity and selectivity for the hydroformylation, including hydroxyhydroformylation, of low molecular weight olefins. To obtain such solids the iron is present on the support in a minor, catalytically effective amount, which can be, for instance, from about 0.001 to 0.1 weight percent of the support, preferably about 0.005 to 0.02 weight percent.

In the preparation of the catalyst composition of the present invention, the iron is provided by compounds of the metal which are at least slightly soluble in some solvent wherein an impregnating solution can be formed. Preferred compounds are the weak field complexes. Suitable sources of the metal can include, for example, halides, e.g., $FeCl_n$, $FeBr_n$, $FeI_n$, where $n$ (here and below) is the available valence of iron; hydrocarbyloxy derivatives of iron, i.e., $Fe(OR)_n$, where R represents alkyl, aryl, aralkyl, and the like groups; dihydrocarbyloxy iron carboxylate, i.e., $(RO)_nFeOOCR'$ where R and R' are as defined above as R; diphosphine complexes, e.g. $(Fe[(C_6H_5)_2PC_2H_4P(C_6H_5)_2]X_2$, where X is a halide. Also available as metal sources are chelates formed by the metal and weak field ligands, such as $\beta$-diketones or $\beta$-keto-carboxylic acid esters and salts of carboxylic acids. Examples of these types of metal sources include β-diketonato iron (II), acetylacetonato iron (II), propylacetonato iron (II), benzoylaetonato iron; chelates from β-ketocarboxylic acid esters; salts of saturated monocarboxylic acids, e.g. iron formate, iron propionate, iron caproate, iron octoate, iron palmitate, iron stearate, iron phenylacetate, iron phenylpropionate, and the like; salts of corresponding unsaturated monocarboxylic acids, e.g. iron acrylate, iron vinyl acetate, and the like; salts of unsaturated dicarboxylic acids, e.g. iron adipate, iron decane-1,10-dicarboxylate, and the like; salts of corresponding unsaturated dicarboxylic acids, e.g., iron miconate and the like; salts of cyclic and aromatic carboxylic acids, e.g., iron cyclohexane carboxylate, iron benzoate, iron phthalates, and the like; and alkoxycarboxylates, e.g. iron dimethoxyacetate and the like. Preferred as the source of iron is iron acetylacetonate.

The solid support of the catalyst of the present invention can be an acidic, silica-based material, e.g., having a D + L activity of at least about 20, preferably at least about 30 when determined according to the method of Birkhimer et al., "A Bench Scale Test Method for Evaluating Cracking Catalysts", Proceedings of the American Petroleum Institute, Division of Refining, Vol. 27 (III), page 90 (1947), and hereinafter referred to as Cat. A. The silica-based support preferably has a substantial surface area as determined by the BET nitrogen absorption procedure (JACS, Vol. 60, pp. 309 et seq.) (1938). The surface area of the support can be at least about 50 square meters per gram, and such surface areas are often up to about 500 or more m²gm., preferably about 150 to 400 m²/gm. It is preferred that the catalyst support be relatively dry to avoid undue reaction with and loss of catalytic promoting materials. Thus, it is advantageous that the support be calcined, e.g., at temperatures of about 600° to 1500° F., or more, to reduce the water content, but such calcination should not be so severe that the support is no longer catalytically-active.

The support component contains other materials in addition to silica which materials, when combined with silica, provide an acidic material as in, for instance, the case of silica-alumina. Often these materials are one or more oxides of the metals of Groups II, III and IV of the Periodic Table. Examples of the composites contemplated herein under the generic designation of silica-based materials are often composed predominantly of, or even to a major extent of, silica. These supports include, for example, silica-alumina, silica-boria, silica-zirconia, silica-magnesia, silica-alumina-zirconia, silica-alumina-thoria, silica-alumina-magnesia, and the like. The silica-based support can contain amorphous or crystalline material such as a crystalline aluminosilicate, for instance, having pore openings in the 6 to 15 Angstrom unit range. The support often contains silica and alumina and such supports, whether naturally-occurring as in acid-treated clays, or a synthetic gel, will frequently contain about 10 to 60, preferably about 15 to 45, weight percent alumina. In addition, such silica-slumina supports can, and preferably do, contain a portion of the alumina as a separate, distinct phase.

A highly preferred catalyst support can be made by combining a silica-alumina hydrogel with a hydrous alumina with or without (preferably without) a crystalline aluminosilicate. An anvantageous hydrous alumina component is, when analyzed by X-ray diffraction of dry samples, either one or a mixture of amorphous hydrous alumina and a monohydrate, e.g., boehmite, of less than about 50 A, preferably less than about 40 A, crystallite size as determined by half-width measurements of the (0, 4, 1) X-ray diffraction line calculated by the Debye-Scherrer equation. The mixture of the catalyst precursor components can be dried, e.g., at about 220° to 500° F. to convert the silica-alumina hydrogel to xerogel form. The dried material can then be calcined, e.g., at a temperature of about 700° to 1500° F., preferably about 800° to 1400° F., to provide the active catalyst support. During calcination, the separate hydrous alumina phase of the mixture is converted to a gamma form or other catalytically-active alumina.

In providing the preferred catalyst support precursor for drying, the components can be combined in any suitable manner or order desired, and advantageously each of the components is in the mixture in finely-divided form, preferably the particles are principally less than about 300 mesh in size. The finely-divided material can have an average particle size of about 10 to 150 microns and can be used to make a catalyst of this particle size which can be employed in a fluidized bed type of operation. However, if desired, the mixture of catalyst support components can be placed in macrosized form, that is, made into particles as by tabletting, extruding, etc., to sizes of the order of about 1/64 inch to ½ inch or more in diameter and about 1/32 inch to 1 inch or more in length, before or after drying or calcination. If formation of the macrosized particles is subsequent to calcination and the calcined particles have been contacted with water, the material can be recalcined.

On a dry basis, the preferred supports of the catalysts of the present invention contain about 45 to 95 weight percent of the amorphous silica-alumina xerogel, about 5 to 55 weight percent of the separately added alumina phase, and about 0 to 50 weight percent of the crystalline aluminosilicate, preferably the proportions of these ingredients are about 75 to 90%, about 10 to 25% and about 0 to 20%, respectively. If present, the crystalline aluminosilicate is usually at least about 1 weight percent, preferably at least about 5 weight percent, based on the dried support. The alumina content from the silica-alumina xerogel and the separate alumina phase is about 20 to 70 weight percent, preferably about 25 to 60 weight percent, based on the dried support. Also, the catalyst support generally contains less than about 1.5 weight percent, preferably less than about 0.5 weight percent, sodium.

The silica-alumina component of the precursor of the preferred catalyst support of the present invention can be a silica-alumina hydrogel which contains about 55 to 90, preferably 65 to 75, weight percent silica and about 10 to 45, preferably about 25 to 35, weight percent alumina, on a dry basis. The silica-alumina can be naturally-occurring or can be synthetically prepared by any desired method and several procedures are known in the art. For instance, an amorphous silica-alumina hydrogel can be prepared by co-precipitation or sequential precipitation by either component being the initial material with at least the principal part of the silica or alumina being made in the presence of the other. Generally, the alumina is precipitated in the presence of a silica gel. It is preferred that the silica-alumina hydrogel be made by forming a silica hydrogel by precipitation from an alkali metal silicate solution and an acid such as sulfuric acid. Then alum solution may be added to the silica hydrogel slurry. The alumina is then precipitated by raising the pH into the alkaline range by the addition of an aqueous sodium aluminate solution or by the addition of a base such as ammonium hydroxide. Other techniques for preparing the silica-alumina hydrogel are well known in the art, and these techniques may be used in the practice of the invention.

The alumina hydrogel which can be combined with the silica-alumina is made separately from the silica-alumina. The alumina hydrogel may be prepared, for example, by precipitation of alumina at alkaline pH by mixing alum with sodium aluminate in an aqueous solution or with a base such as soda ash, ammonia, etc. As noted above, the alumina hydrogel can be in the form of amorphous hydrous alumina or alumina monohydrate, e.g., of up to about 50 A crystallite size as determined by X-ray diffraction analysis. The amorphous hydrous alumina generally contains as much combined water as does an alumina monohydrate. Mixtures of the monohydrate and amorphous forms of hydrous alumina are preferred and often this phase is composed of at least about 25% of each of the separate members.

In preparing the catalyst support, we may separately filter the silica-alumina hydrogel and the hydrous alumina and intimately mix these materials, for instance, by colloidal milling. Although in this particular procedure a low sodium crystalline aluminosilicate can be added after the milling, this ingredient can also be combined before the colloidal milling operation. The mixture is dried, water-washed to acceptable concentrations of, for instance, sodium, and redried in the preferred procedure. The drying, especially the initial drying, is advantageously effected by spray drying to give microspheres.

The crystalline aluminosilicate which can be present in the silica-based catalyst support of the present invention, can have pore openings of 6 to 15 A in diameter, and preferably the pore openings have a diameter of 10 to 14 A. Usually, with a given material, the pores are relatively uniform in size and often the crystalline aluminosilicate particles are primarily less than about 15 microns in size, preferably less than about 10 microns. In the crystalline aluminosilicate the silica-to-alumina mole ratio is often greater than about 2:1 and is usually not above about 12:1, preferably being about 4 to 6:1. The aluminosilicate may be available in the sodium form, and the sodium can be removed before or after the crystalline aluminosilicate is added to the other catalyst support ingredients.

It is preferred to exchange the sodium with ammonium ions, for instance, through contact with an aqueous solution of ammonium chloride or another water-soluble ammonium compound. Subsequently, during drying and/or calcination, the ammonium ion may break down to release ammonia and leave an acid site on the aluminosilicate. On a molar basis, the ammonium or hydrogen ion is usually at least about 10% or even at least about 50%, based on the alumina content of the crystalline aluminosilicate. Suitable replacements for the sodium also include the polyvalent metals of the periodic chart, including the Group II-$a$ and rare earth metals such as cerium, etc. The metals may be present along with the ammonium or hydrogen cations.

The support can also be a naturally-occurring silica-based clay-type mineral, such as kaolin, which contains a major amount of silica and a minor amount of alumina, along with small amounts of other materials, such as sodium oxide, calcium oxide, magnesium oxide, iron oxide, potassium oxide, etc. A typical kaolin clay, after washing and calcining to remove water and other volatile materials which can amount to from about 10 to 20 weight percent of the uncalcined material, can contain from about 50 to 60 weight percent $SiO_2$, about 40 to 50 weight percent $Al_2O_3$, less than about 2 weight percent $Na_2O$ and less than about 1 weight percent of each of CaO, MgO and other metallic oxide impurities. The clay-type support can be fabricated into macrosize form, if desired, of a size of about 1/64 inch to ½ inch or more in diameter and about 1/32 inch to 1 inch or more in length.

The preparation of the overall catalyst composition is preferably conducted by first forming the iron carbonyl compound, which is generally iron pentacarbonyl, e.g., $Fe(CO)_5$. Formation of the iron carbonyl may be effected by dissolving the iron source in a suitable solvent, e.g., ethanol, methanol, benzene, chlorobenzene, or the like, and charging to a reactor. Carbon monoxide gas can then be introduced at a temperature of from about 60° to 400° C., preferably from about 150° to 250° C., and a pressure of from about 500 to 3000 psig., preferably from about 700 to 1800 psig. to obtain the iron carbonyl. The solid support, in finely-divided form, is added to the compound in the solvent and the system is agitated for a time sufficient to affix the compound on the support. Hydrogen gas can be introduced together with the carbon monoxide or separately, in a sequential manner, with the carbon monoxide introduced first. The hydrogen and carbon monoxide are present in a molar ratio ($H_2$:CO) of from about 1:1 to 5:1 and a total pressure of about 500 to 3000 psig. The iron pentacarbonyl can also be formed separately and dissolved in a suitable solvent to which the support can be added and hydrogen at a pressure of from about 500 to 3000 psig., preferably 700 to 1800 psig., introduced. The amount of iron pentacarbonyl dissolved in the solvent is preferably such as to also have a hydrogen to carbon monoxide ratio of from about 1:1 to 5:1, preferably 1.2:1 to 3.5:1.

The solid supported catalyst can also be prepared in situ by charging the metal source, such as iron acetylacetonate, and the support in finely-divided form in a suitable solvent to an autoclave reactor and allowing these components to react under a premixed gas of hydrogen and carbon monoxide of a molar ratio of hydrogen to carbon monoxide of from about 1:1 to 5:1, preferably 1.2:1 to 3.5:1, at a pressure of from about 500 to 3000 psig., preferably about 700 to 1800 psig., and a temperature of from about 150° to 195° C. for about one hour. The resulting supported catalyst system can be separated by removing the liquid phase from the reactor. If desired, the low molecular weight olefin can be charged to the catalyst system before separation and the hydroformylation reaction carried out in the presence of the solvent. After the reaction is completed, the liquid reaction mixture can be separated and removed from the reactor. Alternatively, the catalyst components, support and low molecular weight olefin can be charged simultaneously in a solvent to the autoclave under conditions as set forth above, thus allowing the system to simultaneously undergo formation of the solid supported catalyst system and the hydroformylation of the low molecular weight olefin.

The supported catalyst composition of the present invention is effective for hydroformylation, including hydroxyhydroformylation, of olefinic hydrocarbons, e.g., of 2 to about 16 carbon atoms, preferably 3 to 10 carbon atoms, and is highly desirable for such uses. For example, it is possible to provide alcohols, aldehydes, and the like from aliphatic mono-olefinic hydrocarbons. Of particular interest, however, is the selective activity of the present catalyst composition in the hydroformylation of pentene to form hexanol and hexanal. The selectivity of the catalyst of the present invention is exceptional for this type of reaction, while the activity is high as well, resulting in greater efficiency in producing such alcohols and aldehydes. In the prior art, such alcohols are produced in rather minor amounts. With the present catalyst, it is possible to obtain such alcohols, e.g., n-hexanol and isohexanol as the major product.

Hydroformylation can generally be effected by contacting the olefinically-unsaturated feed with hydrogen and carbon monoxide under pressure and in the presence of the catalyst at a temperature of about 100° to 350° C., preferably about 150° to 200° or 250° C. Elevated temperatures ordinarily can be maintained by the heat of reaction without external heating means. In many cases, it may be necessary to control the temperature by cooling, as for example, by circulating a cooling medium through heat exchange tubes in the reactor. Pressures of up to about 3000 or more psig, preferably about 700 to 1800 psig, are suitable with the catalyst composition of the present invention. The amount of catalyst composition used in the reaction is that sufficient to effect hydroformylation or hydroxyhydroformylation of the feed and often the olefin feed contacts the catalyst at the rate of about 1 to about 20, preferably 1 to 10, WHSV (weight of olefin per weight of catalyst per hour). The process is applicable to continuous processing, e.g., with a catalyst slurry or a fixed bed, as well as batch processes. The hydrogen and carbon monoxide are usually provided to the reaction zone in a molar ratio of hydrogen to carbon monoxide from about 1.1:1 to 5:1, preferably from about 1.2:1 to 3.5:1. Preferably, the materials are added to the reactor as a premixed gas.

The preparation of an acidic silica-alumina support of this invention is illustrated by Examples I–III, and the support contains a separate phase of alumina.

EXAMPLE I

An alumina hydrogel is prepared as follows:

In a tank containing 5700 gallons of water at 85° F., are dissolved 300 lbs. of soda ash. When the soda ash had been dissolved, 180 gallons of a 39% concentration aqueous sodium aluminate solution are pumped into the tank in about a 15-minute period. The contents of the tank are at about 84° F. Six-hundred gallons of aqueous aluminum sulfate of 7.8% concentration, as $Al_2O_3$, are added to the admixture over an 80-minute period with water of dilution in conjunction with, and in addition thereto, diluting the reaction mass at a rate of 25 gallons per minute.

The pH of the resulting aqueous reaction mass is adjusted to 8.0 with about 75 gallons of 39% concentration aqueous sodium aluminate solution which, while being added, is also diluted continuously with water at a rate of 35 gallons per minute over a 7½ minute addition period. The contents of the tank are heated to about 100° F., and pumped to storage.

The precipitated, hydrated alumina is thereafter filtered on a large gel filter. The filtered product is partially purified by a one-cycle, water-wash on the filter on which it is collected. This filter is a string vacuum type drum filter with a built-in water spray nozzle directed toward the filter drum. Material on the drum is contacted with water as the drum rotates past the nozzle. After washing, the wet alumina hydrogel is stripped from the drum. This hydrogel analyzes about 50% boehmite having a crystallite size of about 35 A, and 50% amorphous hydrous alumina as determined by X-ray diffraction on dried samples.

EXAMPLE II

A silica-alumina hydrogel is prepared by the following technique:

To a batch tank is added 4,275 gallons of water preheated to 90° F., and 865 gallons of sodium silicate solution (28.8 weight percent $SiO_2$, 40–41.5 Baume at 68° F. and $Na_2O:SiO_2$ ratio of 1:3.2) is added. The batch is stirred for five minutes. The concentration of the sodium silicate, as $SiO_2$, in the batch is 6.3 weight percent.

With the batch at 90° F., 302 gallons of 34.5 weight percent sulfuric acid solution at 182° F. are added over a period of 45 minutes. The gel forms about 35 minutes after acid addition is begun. Then the pH is adjusted to 8.0–8.5. The batch is agitated for ten minutes.

Then 715 gallons of alum (7.8 weight percent, as $Al_2O_3$) is added to the gel over a period of about 36 minutes. The batch is agitated for an additional five minutes whereupon 205 gallons of sodium aluminate solution (24.4 weight percent as $Al_2O_3$) diluted in 1080 gallons of water is added over a period of 17 minutes. After all the sodium aluminate is added, the pH is checked. It should be between 5.0 and 5.2. The alumina content of the silica-alumina hydrogel is 30–31%.

EXAMPLE III

The silica-alumina hydrogel product of Example II and 1740 gallons of the alumina hydrogel filter cake of Example I are mixed together for one hour. The finished batch has a pH of 5.5 to 5.6 and a temperature of about 110° F. The aqueous gel mixture is then pumped to a dewatering filter and the filter cake from said dewatering filter and a portion of aqueous gel are blended to give a gel slurry of about 14 weight percent solids. A portion of this hydrogel mixture was slurried, as a thick flowable paste, with a "Lightnin" stirrer fitted with a cage-beater and a propellor, for about 10 minutes to give a thorough dispersion. The product was stirred one minute at 14,500 rpm, in a Waring Blender and dried in a laboratory spray-drier. The spray-dried material was washed with water to acceptable impurity levels and dried at 230° F. The washed and dried material analyzed 0.08% $SO_4$ and less than 25 ppm $Na_2O$. The dried material as such was used as the catalyst support, as were extruded forms thereof and tablets (pellets) having diameters of about 1/8 inch and lengths of about ⅛ to ½ inch. Before use the catalyst support was calcined in a muffle furnace by raising the temperature by 300° F. per hour until 1350° F. was reached. This temperature was then held for three hours. The calcined particles had a surface area of about 320 to 340 square meters per gram.

Example IV illustrates the preparation of the catalyst compositions of this invention on the silica-based support.

EXAMPLE IV

A 300 cc. stainless steel autoclave, equipped with a magnetic stirrer was used as a reactor throughout the present work. The calcined, spray-dried microspheroids of Example III in the amount of 12 g. and having the following distribution:

| | |
|---|---|
| 0–10 $\mu$ | 0.0 wt. % |
| 10–20 $\mu$ | 0.5 |
| 20–40 $\mu$ | 20.3 |
| 40–80 $\mu$ | 67.3 |
| >80 $\mu$ | 12.3 | were introduced to a red solution which had 1.9 m moles ferric acetylacetonate dissolved in 70 ml benzene in the autoclave. The reactor was purged with hydrogen for about 15 minutes. Pentene-1, taken as a typical olefin, was hydro- and hydroxyhydroformylated by reaction with carbon monoxide and hydrogen in the presence of a catalyst having hydrido iron carbonyl on the support of Example III. The supported catalyst was prepared in situ in the autoclave and a series of batch runs intermittently made with this solid catalyst over a prolonged period. Pentene-1 (30 ml) was introduced to the mixed system of ferric acetylacetonate and microspheroids in benzene, and the reactor was pressured with a premixed gas ($H_2$:CO molar ratio of 1:1) to 510 psig and then to 800 psig with hydrogen at 78° F. to yield an $H_2$:CO molar ratio of 2:1. The system was heated by an external heater for about an hour. At this stage the temperature and pressure of the reactor were 260° F. and 1060 psig, respectively, and an initial slow pressure drop was noticed. The reactor was vigorously agitated, and maintained under 1100–1050 psig at 260°–330° F. for about 2 hours. Heating was discontinued and the reactor was allowed to cool overnight. The pressure of the reactor was 660 psig at room temperature. A yellow reaction mixture was removed from the reactor through a filter attached to the bottom of the reactor. The product was analyzed by means of gas chromatographic techniques.

About 80% of the feed was reacted to give almost exclusively hexanols (23.3% isohexanol, 69.2% n-hexanol and 0.2% isohexanal, 0.8% n-hexanal and 6.4% unidentified and heavy products. During this run, the catalyst species interacted with the supporting base to generate the solid catalyst. In short, the acidic silica-alumina material used in this run functions both as an effective support to give a solid catalyst and as a co-catalyst. In addition to the hydroformylation, the present solid catalyst is employable in gas and liquid phase isomerization (double bond migration) and hydrogen transfer reactions.

The solid phase left inside of the reactor from the first run was rinsed with fresh portions of benzene, and was saved for four more consecutive runs.

Due to the characteristic nature of the solid, acidic, silica-based support to impregnate some liquid into its microspheroid structure, quantitative removal of the reaction mixture from the reactor was impossible, and thus some contamination from preceding runs was unavoidable throughout consecutive batch runs.

EXAMPLE V

In this run, the reactor was pressured with a premixed gas ($H_2$:CO molar ratio of 1:1) to 500 psig and then to 750 psig with hydrogen to yield an $H_2$:CO molar ratio of 2.1 immediately after 30 ml pentene-1 was fed to the washed solid catalyst of Example IV along with 25 ml benzene. Heating of the reactor was controlled to reach a temperature, 322° F., from 78° F. in about an hour. The maximum pressure, 1105 psig, exhibited at this stage, dropped to 850 psig when the reactor was kept at 322°–340° F. for a 3½ hour period. A clear light yellow reaction mixture was discharged from the reactor. The apparent conversion of the pentene-1 feed was 92% and the product was composed of 1.2% isohexanal, 6.3% n-hexanal, 23.9% isohexanol, 63.6% n-hexanol and 5.0% unidentified and heavy products. The results obtained from this run clearly demonstrate that the catalyst species, hydridoiron carbonyl, is firmly supported on the solid, acidic, silica-based support base, and that the resulting supported solid catalyst exhibits catalytic activity for hydro- and hydroxyhydroformylation of pentene-1 at a high level.

EXAMPLE VI

In this run, 4.0 m moles of tri-n-butylphosphine in 23 ml benzene was fed to the solid catalyst of Example V, which aged for 22½ hours from the two preceding runs. After 28 ml of pentene-1 was introduced to the reactor, the system was again pressured to 800 psig to give a final molar ratio of $H_2$/CO of ½. After an initial heating period (1½ hours), the reactor was kept under 1080–1040 psig at 337° F. for about 4½ hours. Conversion of the feed was 43%, which was decreased consideraly from the preceding runs. Details of the reaction conditions and product distributions are given below in Tables I and II. This may be attributed to the introduction of tri-n-butylphosphine rather than the aging pattern of the solid catalyst. This result is opposite to that obtained from the homogeneous system iron pentacarbonyl and triphenyl phosphine in benzene reported in J.A.C.S. 3133 (1968). The same reaction was repeated (with the catalyst aged from the first run) in both second and third runs in the absence of solvent. Details of the reaction conditions and product distributions are shown below in Tables I and II. The catalytic activity for the hydroxyhydroformylation of pentene-1 was well maintained in these runs. The tan colored solid catalyst left from these runs was analyzed for iron and phosphorus. About 1.5 m moles iron and 1.9 m moles phosphorus were still retained on the solid, acidic, silica-based support base. While the addition of tri-n-butylphosphine in the benzene solvent detracted from the hydroformylation activity of the catalyst, the hydrido-iron carbonyl supported catalyst of this invention may contain other ingredients which may improve the performance of the catalyst.

TABLE I

| | | Catalyst Composition | | | | | Reaction Conditions | | | |
|---|---|---|---|---|---|---|---|---|---|---|
| Example No. | Run No. | Iron acetyl-acetonate mm | Tributyl-phosphine mm | Support g | Benzene Solvent ml | Catalyst Aged Hrs. | Pressure psig | Temperature ° F. | Reaction Time Hrs. | $H_2$/CO |
| VI | 1st | 1.9 | 4.0 | 12 | 23 | 22-½ | 1080–1040 | 337 | 4-½ | 2 |

TABLE I-continued

| Example No. | Run No. | Catalyst Composition | | | | Catalyst Aged Hrs. | Reaction Conditions | | | $H_2/CO$ |
| --- | --- | --- | --- | --- | --- | --- | --- | --- | --- | --- |
| | | Iron acetyl- acetonate mm | Tributyl- phosphine mm | Support g | Benzene Solvent ml | | Pressure psig | Temperature °F. | Reaction Time Hrs. | |
| | 2nd | 1.9 | <4.0 | 12 | 0 | 53 | 1050–910 | 370–420 | 1–½ | 2 |
| | 3rd | 1.9 | <4.0 | 12 | 0 | 91 | 1100–1060 | 280–300 | 3–⅓ | 2.3 |

TABLE II

| Example No. | Run No. | Feed, pentene-1 g. | Conversion % | Product Distribution, % | | | | |
| --- | --- | --- | --- | --- | --- | --- | --- | --- |
| | | | | isohexanal | n-hexanal | isohexanol | n-hexanol | Unknown + Heavy |
| VI | 1st | 17.9 | 43 | 2.1 | 0.2 | 15.7 | 44.4 | 37.7 |
| | 2nd | 19.2 | 53 | 3.0 | 1.0 | 18.7 | 52.1 | 25.2 |
| | 3rd | 21.3 | 35 | 3.6 | 4.9 | 19.7 | 56.3 | 15.5 |

The invention claimed is:

1. In the process for the hydroformylation of olefin hydrocarbons of 2 to about 8 carbon atoms at a temperature of from about 100° to 350° C. at a pressure of from about 700 to about 1800 psig in the presence of an iron catalyst, the improvement which consists essentially of conducting said hydroformylation in contact with an active catalyst formed under hydroformylation conditions, said catalyst comprising a major amount of a solid acidic calcined support comprised of about 45 to 95 weight percent amorphous silica-alumina, said support containing a separate phase of alumina constituting about 5 to 55 weight percent of said support, the total alumina content of said support being about 20 to 70 weight percent, said separate phase alumina resulting from the calcination of a mixture of amorphous hydrous alumina and alumina monohydrate, said catalyst being initially introduced in a form consisting essentially of said major amount of support and a minor amount of iron constituting from about 0.001 to about 0.1 weight percent of the catalyst.

2. In a process for the hydroformylation of an aliphatic monoolefin hydrocarbon of 2 to about 8 carbon atoms, the improvement which comprises conducting said hydroformylation reaction in contact with a catalyst composition which comprises a major amount of a solid, acidic, silica-based support of silica-alumina containing a separate phase of alumina, the total catalyst composition containing from about 0.001 to about 0.1 weight percent of iron, said support comprising 45 to 95 weight percent amorphous acidic silica-alumina, said support comprising 5 to 55 weight percent of said separate phase of alumina, said separate phase alumina resulting from the calcination of a mixture of amorphous hydrous alumina and alumina monohydrate, the total alumina content of said support being about 20 to 70 weight percent, said support being prepared by mixing together a separate phase alumina hydrogel with a silica-alumina hydrogel, dewatering the mixture to provide a gel slurry of about 14 weight percent solids, spray-drying said slurry, washing the spray-dried material, pelletting the washed material, and calcining the pellets at about 1350° F. for about three hours to provide calcined particles, said hydroformylation being conducted at a temperature of from about 100° to 350° C. at a pressure within a range from about 700 to about 1800 psig at an hourly velocity of weight of aliphatic monoolefin hydrocarbon per weight of catalyst of from about 1 to about 10, the hydrogen to carbon monoxide mol ratio being from about 1:1 to about 5:1.

3. The process of claim 1 wherein said olefin is pentene.

* * * * *